United States Patent [19]

Bailey

[11] Patent Number: 5,501,596
[45] Date of Patent: Mar. 26, 1996

[54] AUTOCLAVABLE DENTAL SCALER HANDPIECE

[75] Inventor: Ronald L. Bailey, Harvester, Mo.

[73] Assignee: Young Dental Manufacturing Company, Inc., Earth City, Mo.

[21] Appl. No.: 281,452

[22] Filed: Jul. 27, 1994

[51] Int. Cl.⁶ .................... A61C 1/07; A61C 1/08
[52] U.S. Cl. .................. 433/86; 433/119; 433/126
[58] Field of Search .................. 433/86, 118, 119, 433/126, 29; 604/22; 607/97

[56] References Cited

U.S. PATENT DOCUMENTS

| 3,082,394 | 3/1963 | Hahn et al. ................ 339/16 |
| 3,110,537 | 11/1963 | Poetzsch et al. ........... 339/16 |
| 3,656,781 | 4/1972 | Paine et al. ................ 285/3 |
| 3,673,541 | 6/1972 | Volinskie .................. 339/16 R |
| 3,992,565 | 11/1976 | Gatfield ................. 174/15 WF |
| 4,080,737 | 3/1978 | Fleer ....................... 32/22 |
| 4,182,038 | 1/1980 | Fleer ..................... 433/126 X |
| 4,310,310 | 1/1982 | Bailey .................... 433/126 |
| 4,398,885 | 6/1983 | Loge et al. .............. 433/126 |
| 4,406,621 | 9/1983 | Bailey .................... 433/126 |
| 4,568,284 | 2/1986 | Stankiewicz ............. 433/126 |
| 4,578,034 | 3/1986 | Shibata et al. ........... 433/29 |
| 4,957,483 | 9/1990 | Gonser et al. ........... 433/126 X |
| 5,039,304 | 8/1991 | Heil ...................... 433/126 |
| 5,395,240 | 3/1995 | Paschke et al. ........... 433/86 X |

OTHER PUBLICATIONS

ULTRACLAVE™Scaler Operating Instructions, 1988.

Primary Examiner—Nicholas D. Lucchesi
Attorney, Agent, or Firm—Polster, Lieder, Woodruff & Lucchesi

[57] ABSTRACT

A dental scaler is provided which has a control unit and a handpiece assembly linked to the control unit by a conduit carrying fluid and electrical power. The handpiece assembly includes a conduit connector secured to an end of the conduit remote from the control unit and an autoclavable handpiece removably securable to the conduit connector. The connector and handpiece have slidably connectable bodies, each having mating fluid and electrical connectors. The handpiece connector body includes a check valve to prevent rearward flow of water. The conduit connector body includes a check valve and a double fluid tight seal. The use of the two check valves and two seals reduces the possibility of fluid leaking from the back of the handpiece or from the connector. The conduit connector body is received in a sleeve of the handpiece. The connector has a finger which is received in an axial slot of the handpiece sleeve. The finger and slot form a size-on-size fit to frictionally hold the conduit connector and handpiece together.

17 Claims, 5 Drawing Sheets

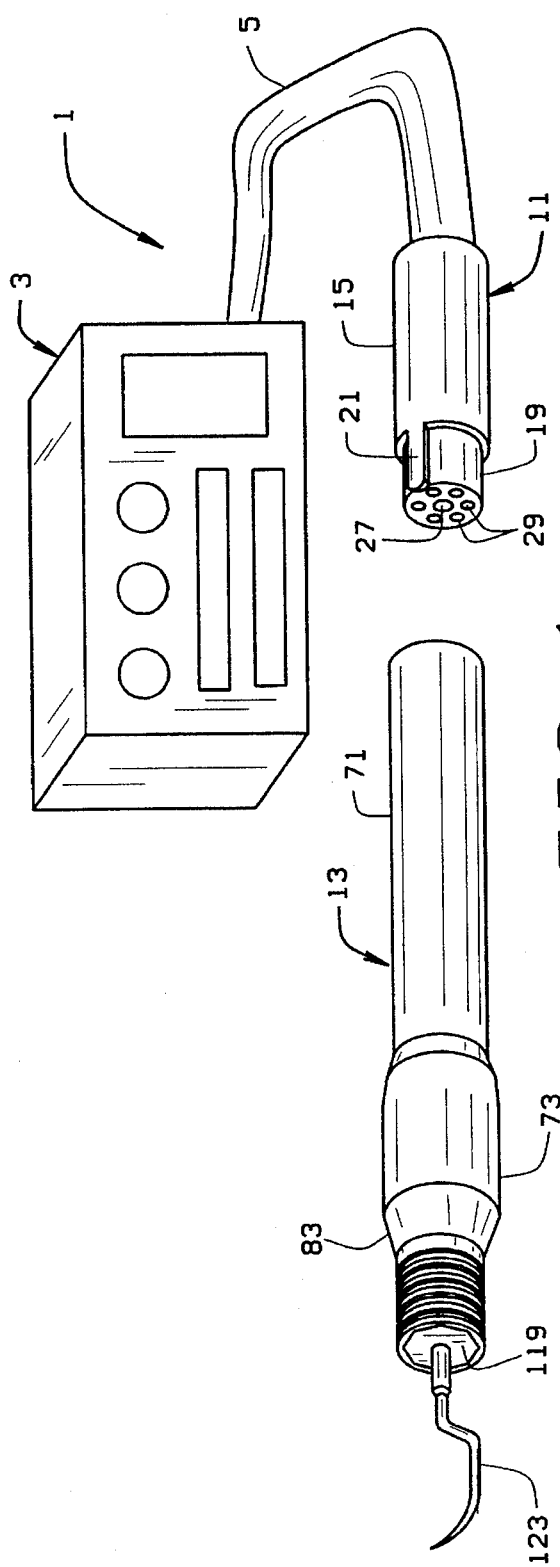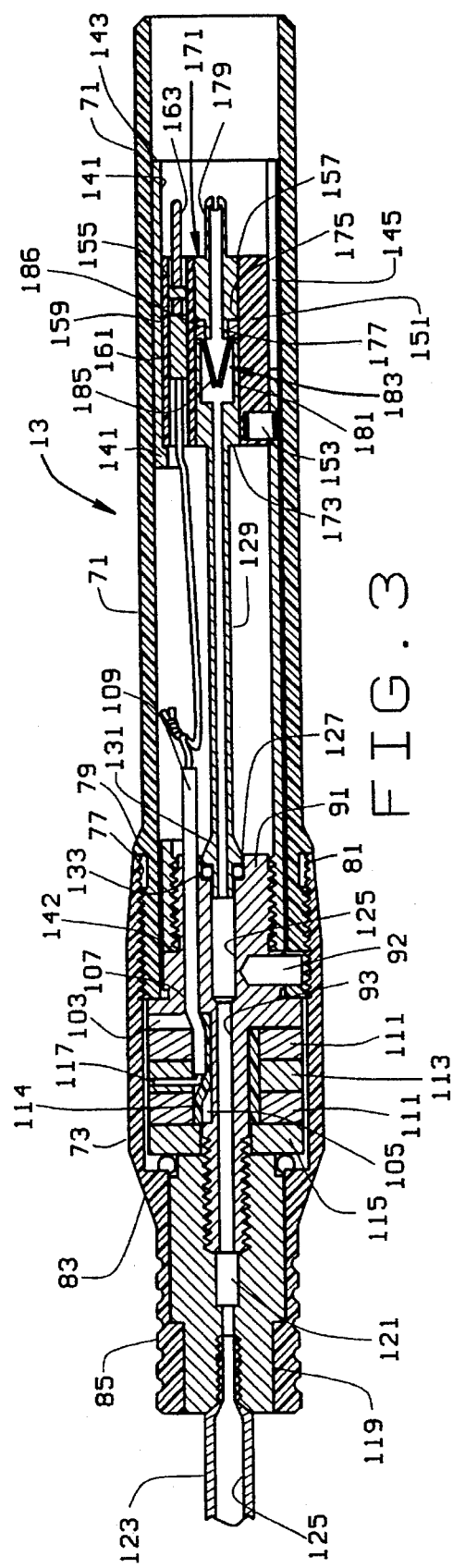

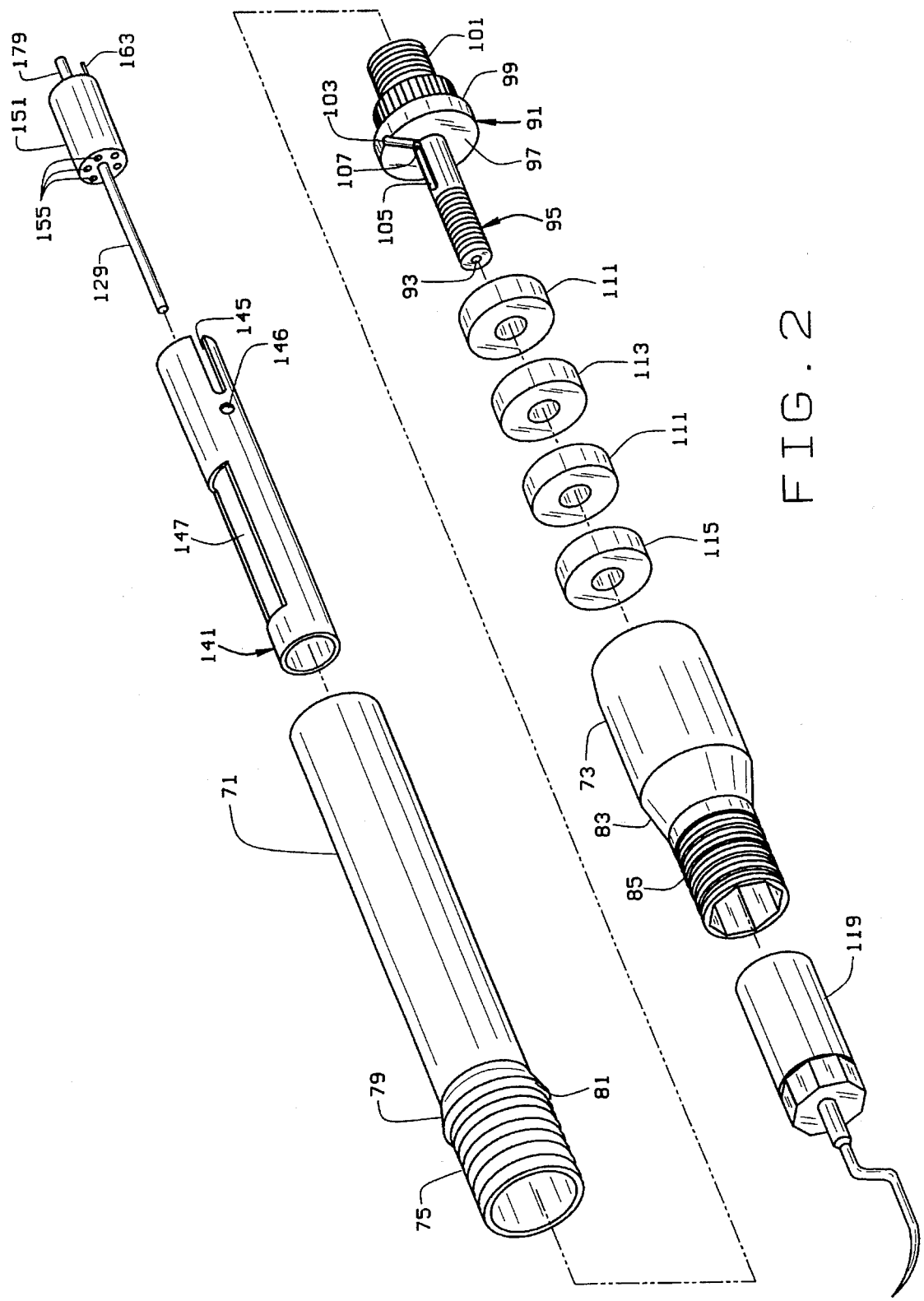

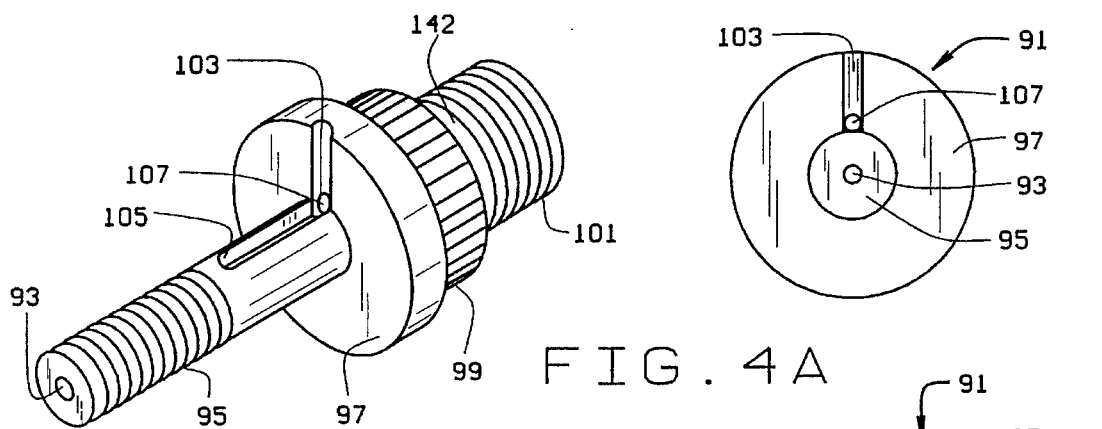
FIG. 4
FIG. 4A
FIG. 4B
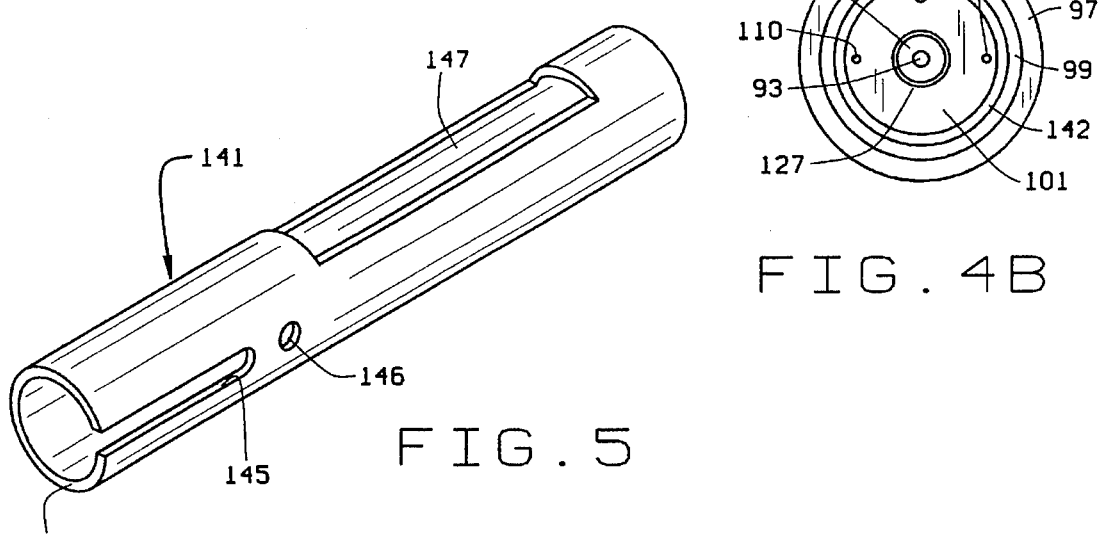
FIG. 5
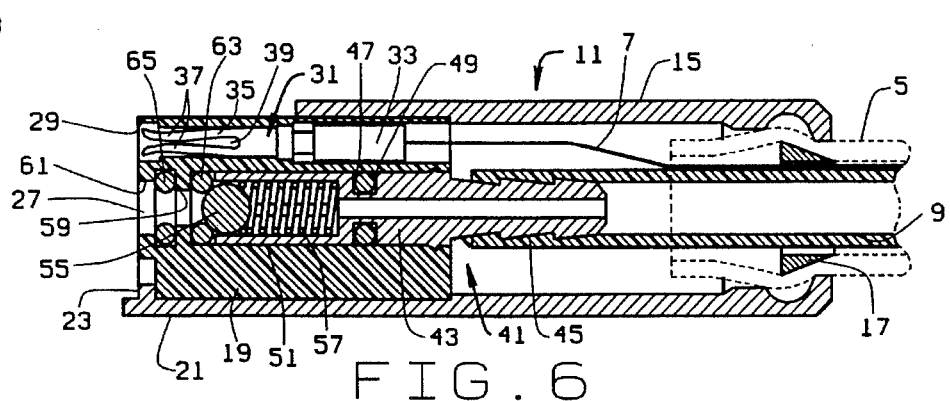
FIG. 6
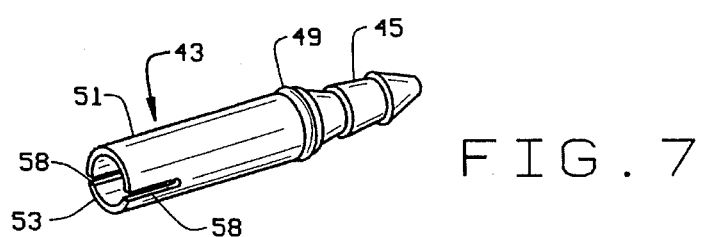
FIG. 7

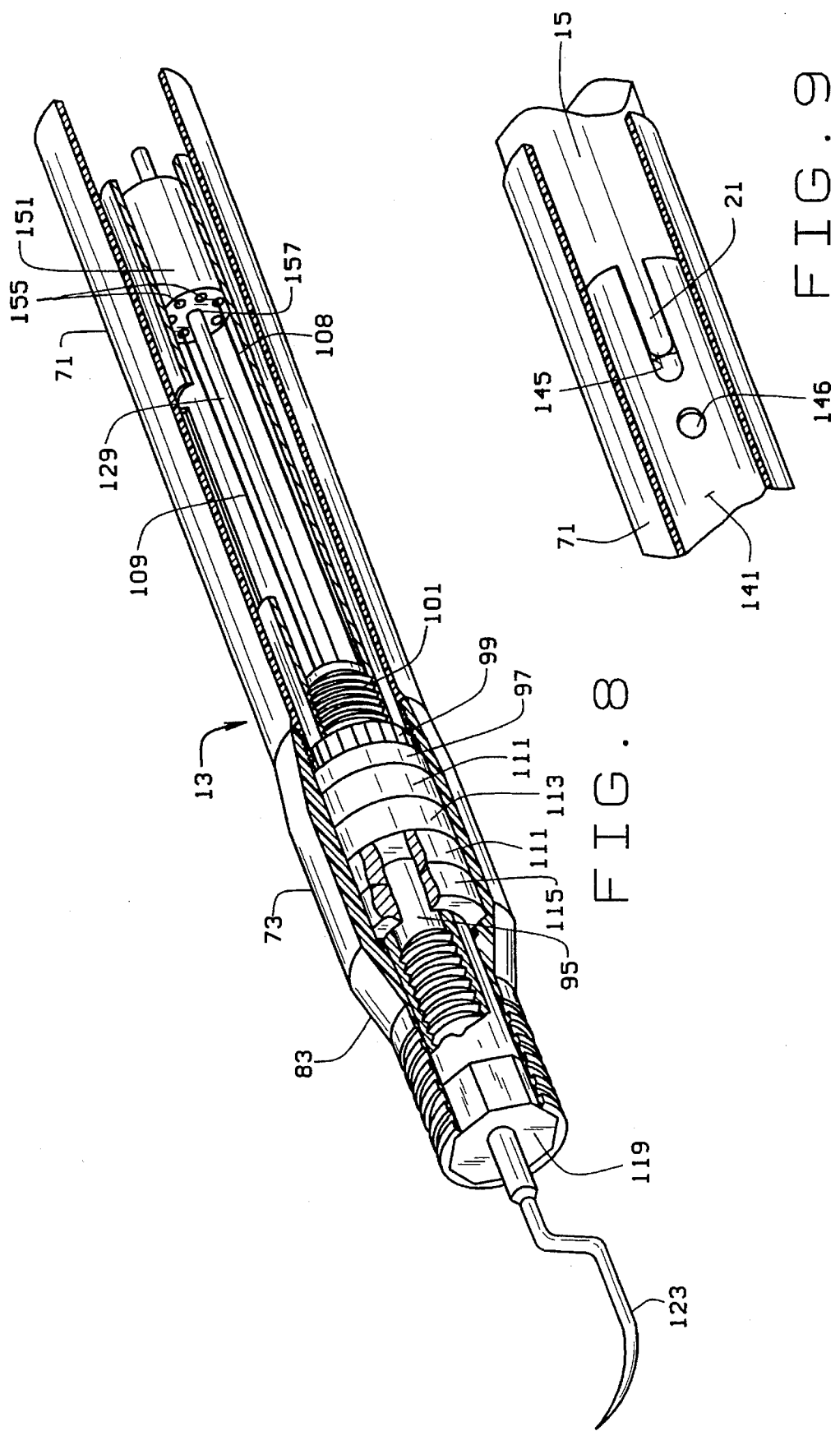

AUTOCLAVABLE DENTAL SCALER HANDPIECE

BACKGROUND OF THE INVENTION

This invention relates to dental scalers, and in particular to autoclavable scaler handpieces.

Dental scalers are often used by dentists and hygienists to remove plaque from a patient's teeth. When the scaler is used, operating fluids, such as blood and saliva, can accumulate on the scaler handpiece. Scalers typically operate by exciting piezoelectric elements which cause the scaler tip to vibrate or oscillate at a high rate of speed. A water flow is generally used to cool the tip. Because a water flow is used, it is possible for the operating fluids to enter the handpiece. Thus, to properly clean the handpiece before using it on another patient, it should be autoclaved, to sterilize the inside, as well as the outside, of the handpiece.

To autoclave the handpiece, the handpiece must be removable from the scaler control box. The connector which connects the scaler to the control box must be operable to prevent the water from contacting the electrical elements of the scaler when the handpiece is being connected to, or disconnected from, the control box. Some scalers use a suck-back system to keep the fluid from leaking. This system pulls the water back into the handpiece. This is undesirable because it will also suck operating fluids into the handpiece which will contaminate the interior of the handpiece. This is obviously undesirable.

SUMMARY OF THE INVENTION

One object of the present invention is to provide an autoclavable scaler handpiece.

Another object is to provide a connector which will removably connect the handpiece to a control box of the scaler.

Another object is to provide such a connector which will substantially prevent water from contacting the electrical connectors of the scaler when the handpiece is connected to, and disconnected from, the control box.

Another object is to provide a connector which will not pull contaminants rearwardly into the handpiece.

Another object is to provide such a connector which is contained, in part, within the handpiece.

Another object is to provide such a connector which is easy to use and is reliable.

These and other objects will become apparent to those skilled in the art upon studying the following description in light of the accompanying drawings.

In accordance with the invention, generally stated, a dental scaler includes a control unit and a handpiece assembly connected to the control unit by a conduit carrying fluid and electrical power. The handpiece assembly includes a conduit connector secured to an end of the conduit remote from the control unit and an autoclavable handpiece removably securable to the conduit connector. The conduit connector has a housing containing a body which extends forwardly of the connector housing. The body contains an electrical socket and a fluid path. A check valve is positioned in the fluid path and is normally biased closed to prevent forward flow of water through the connector.

The autoclavable handpiece includes a connector body having an electrical plug matable with the conduit connector socket and a fluid needle which is insertable into the conduit connector valve. A transducer body is housed in the handpiece forwardly of the handpiece connector body. A piezoelectric crystal and a scaler tip are mounted to the transducer body. The crystal is electrically connected to the handpiece electrical plug, and the tip is in fluid communication with the fluid needle and in operational contact with the crystal to be vibrated by the crystal when the crystal is activated.

The transducer body and piezoelectric crystal are preferably housed in a shield from which the scaler tip extends. An outer sleeve extends rearwardly from the shield. The handpiece connector preferably is housed in an inner sleeve which is slidably received in the outer sleeve and connected to the back of the transducer body. The inner sleeve extends rearwardly, beyond the handpiece connector, and the outer sleeve extends rearwardly beyond the inner sleeve.

The inner and outer sleeve are sized so that the conduit connector body may be slidably received in the inner sleeve. The inner sleeve has an axial extending slot which slidably receives the connector housing finger. The slot and finger are sized to create a size-on-size fit to frictionally hold the handpiece to connector. Preferably, the inner sleeve is made from an autoclavable plastic which will expand slightly when the connector housing finger is inserted into the inner sleeve slot.

The fluid connection between the handpiece connector body and the conduit connector body provides two separate fluid tight seals forwardly of the valve to ensure that there will be a fluid tight seal before the connector valve is opened when the handpiece and connector are joined, and a fluid tight seal when the connector valve is closed as the handpiece and connector are separated. A check valve is also positioned in the handpiece connector body to prevent the rearward flow of fluid from the back of the handpiece. The two valves and the double fluid tight seal serve to reduce the possibility of fluid leaking on a patient or an operator and to reduce the possibility of fluid migrating to a live electrical plug.

BRIEF DESCRIPTION OF THE DRAWINGS

FIG. 1 is a perspective view of a dental scaler of the present invention;

FIG. 2 is an exploded view of a handpiece of the scaler;

FIG. 3 is a cross-sectional view of the handpiece;

FIG. 4 is a perspective view of a transducer body of the handpiece;

FIGS. 4A and 4B are front and back elevational views of the transducer body;

FIG. 5 is a perspective view of an internal sleeve of the handpiece;

FIG. 6 is a cross-sectional view of a connector of the scaler;

FIG. 7 is a perspective view of a valve body of the connector;

FIG. 8 is a perspective view, partially cut away, of the handpiece;

FIG. 9 is a perspective fragmentary view, partially cut away, showing the connection between the connector and the handpiece.

DESCRIPTION OF THE PREFERRED EMBODIMENT

Figure 10:
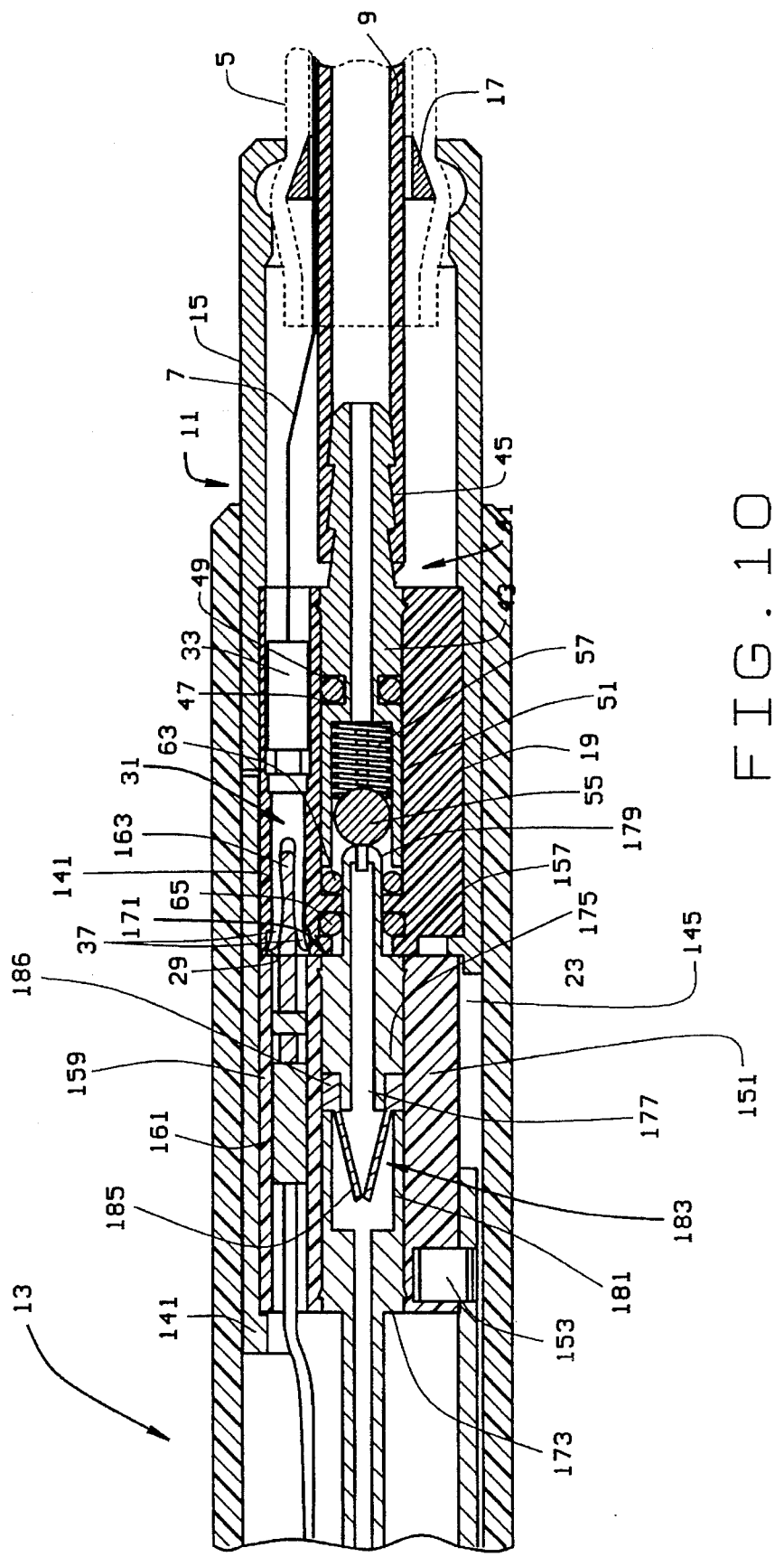
FIG. 10 is a cross-sectional view of the handpiece and the connector when assembled.

Referring initially to FIG. 1, a dental scaler 1 of the present invention includes a control unit 3 is used to control the operation of the scaler. A conduit 5 carrying electrical lines 7 and a fluid line 9 (FIG. 6) extends from the control unit to a conduit connector 11 to deliver fluid and electrical power to a handpiece 13. Handpiece 13 is removably connectable to the conduit connector 11. Handpiece 13 may be removed from the connector so that the handpiece may be autoclaved to fully and properly sterilize the handpiece after each use.

Turning to FIG. 6, the conduit connector 11 has a shell or housing 15 having a forward opening and a rear opening. The conduit 5 is passed into the rear opening of the shell 15 and is held in the shell by an annular strain relief wedge 17. A connector body 19 is received in the forward opening of shell 15 and extends forwardly of the shell, as best seen in FIG. 1. Shell 15 has an arm 21 extending forwardly over connector body 19. A finger 23 extends radially inwardly from arm 21 to serve as a stop to properly position body 19 in shell 15. Preferably, arm 21 extends slightly beyond finger 23.

Connector body 19 has a central, axially extending through-bore 27 and a plurality of axially extending through-bores 29 spaced radially from bore 27. Bores 29 preferably define a circle concentric with central bore 27 as seen in FIG. 1.

An electrical connector 31 is received in one of the bores 29. Connector 31 has a back portion 33 to which wire 7 is operatively connected. A front portion 35 has a pair of slightly flexible arms 37 defining a socket 39. Additional electrical connectors may be placed in other of the bores 29 as needed. Preferably, there are three electrical connectors 31.

A check valve 41 is received in central bore 27. Valve 41 includes a valve body 43 having a hollow barbed stem 45 which is received in fluid hose 9 to secure hose 9 to the valve body. An outer, annular channel 47 is formed forwardly of stem 45 to receive an O-ring 49 which seals against the surface of bore 27. The forward end 51 of valve body 43 defines a guide chamber 53 which receives a valve member or ball 55 which is biased forwardly by a spring 57. Ball 55 has a diameter only slightly smaller than that of chamber 53. Slots 58 are therefore formed in body 43 around the ball 55 to allow fluid to flow around the ball 55 when the valve is opened. Although slots 58 are preferably formed to extend though the wall of body 43, grooves would work as well.

Connector body bore 29 defines an inner flange 59 and an outer flange 61 both of which extend radially inwardly. Valve body 43 is received in bore 27 rearwardly of inner flange 59. An O-ring 63 is positioned between the forward edge of valve body 43 and a rear surface of inner flange 59. Spring 57 biases ball 55 forwardly against O-ring 63, and the O-ring thus serves as a valve seat. A second O-ring 65 is received between the inner and outer flanges 59 and 61.

Handpiece 3 is shown in detail in FIGS. 2–5. The handpiece is, as will be described, removably securable to conduit connector 11 and is made of autoclavable materials. Thus, after each use, the handpiece can be removed from the connector so that it may be properly sterilized in an autoclave. If the handpiece were not removable, it could not be autoclaved, and could be cleaned only by wiping down the handpiece. This, however, cannot properly sterilize the handpiece because any contaminants contained within the handpiece would not be neutralized, as is necessary for a completer sterilization of the handpiece. If the connection where made between the conduit 5 and the controller 3, then the conduit 5, the fluid tube 9, and the electrical wire 7 would all have to be made of flexible materials which could withstand the heat of an autoclave. Such a unit is difficult to make. Hence, connector 11 is preferably placed at the end of the conduit 5 and the only part of scaler 1 that is autoclaved is the handpiece 13, which is the only portion of the scaler that is placed, in part, in a patient's mouth, and thus the only part that must necessarily be autoclaved.

Handpiece 13 includes an outer sleeve 71 having a shield 73 at its forward end. Sleeve 71 and shield 73 are both preferably made from a nylon such as is commercially available from The Polymer Corporation of Reading, Pennsylvania under the name NYLATRON. NYLATRON is capable of withstanding the environment in an autoclave without being degraded. The sleeve and shield could also be made from other autoclavable materials, such as metal or other plastics.

Sleeve 71 has external threads 75 at a forward end and shield 73 has internal threads 77 (FIG. 3) at a back end so that sleeve 71 and shield 73 can be threadably connected. Sleeve 71 preferably has a ramped surface 79 with a generally radially extending forward edge 81 behind threads 75. Edge 81 functions as a stop to prevent the sleeve from being threaded too far into shield 73. Ramp 79 provides for a smooth transition between sleeve 71 and shield 73. The wider diameter provides an area of the handpiece that may be easily grasped by an operator. Shield 73 narrows, as at 83, to a forward nose portion 85 which has the same outer diameter as sleeve 71. Nose 85 is preferably provided with knurls, to make grasping of the handpiece at the nose easier.

A transducer body 91, made preferably of stainless steel, is housed in part in shield 73 and in part in sleeve 71. Body 91 is slidably received in sleeve 71 and is provided with a pin 92 (FIG. 3) which passes radially through a forward part of sleeve 71 into a rear portion of transducer body 91 to prevent rotation of the transducer body with respect to sleeve 71. Transducer body has an axial bore 93 which extends between the front and back surfaces of the body. Body 91 has a forward nose portion 95 which extends forwardly from the center of a generally flat disk 97. Disk 97 has an circumference that is preferably larger than the inner diameter of sleeve 71. The back of disk 97 thus sits against the forward edge of sleeve 71. A shoulder 99 extends rearwardly from disk 97. Shoulder 99 has a diameter slightly smaller than that of sleeve 71 and is received in the forward part of the sleeve. An externally threaded portion 101, which is smaller in diameter than shoulder 99, extends rearwardly from shoulder 99 into sleeve 71.

A radial groove 103 is formed in the forward surface of disk 97. An axial groove 105 extends partially along nose 95 from groove 103. An axial bore 107 extends through disk 97 and shoulder 99 from groove 105, so that an insulated wire 109 (FIG. 3) may be passed through transducer body 91. Two smaller diameter bores 110 in the rear surface of threaded portion 101 receive ground wires 108 (FIG. 8).

An annular piezoelectric crystal 111 (FIGS. 2 and 3) is received on nose 95. Preferably, there are two crystals 111 which are separated by an electrically conductive washer 113. Preferably, one of the crystals 111 abuts disk 97. An insulator 114 (FIG. 3) surrounds transducer nose 95, at least in part, to electrically isolate nose 95 from conductive washer 113. A second washer 115, which is preferably a compression washer, is placed against the forward face of the second crystal 111. Washer 113 (FIG. 3) has a radial bore 117 which receives a bare end of wire 109. Washer 113 thus serves to transmit electrical energy through the two crystals to activate the crystals. Grooves 103 and 105 are provided to form a passage way through which wire 109 may pass, so that crystals 111 and washer 113 may be easily slid on to nose 95. A transducer nut 119 (FIG. 3) is threaded onto the end of nose 95 to hold the crystals 111 and washers in place. Nut 119 is enclosed by nose 85 of shield 73. Nut 119 has a through bore 121 in communication with bore 93 of transducer body 91.

The forward end of bore 93 is threaded so that a scaler tip 123 may be screwed into the nut 119. Tip 123 has a fluid passageway 125 which is in communication with the bores of nut 119 and body 93. As is known, when the piezoelectric crystals are energized, by passing current through wire 109, the crystals begin to vibrate. The construction of the transducer body allows the vibration of the crystals to be transmitted to the scaler tip 123 so that the tip will vibrate.

The transducer body bore 93 preferably is stepped to become wider, as at 125, at a rear part of the body 91. Bore 125 is counter-bored as at 127 (FIG. 3) to receive a fluid tube 129. Tube 129 is received in bore 125. Tube 129 is flaired, as at 131, to retain an O-ring 133 in counter-bore 127. O-ring 133 is placed in the counter-bore, between a forward flat surface of tube flair 131 and the shoulder of counter-bore 127 to provide a fluid tight seal between the tube 129 and transducer body 91.

An internal sleeve 141, having a diameter slightly smaller than that of the outer sleeve 71, is received within sleeve 71. Sleeve 141 is also made of NYLATRON, or another autoclavable material. Internal sleeve 141 is internally threaded at its forward end to be threaded onto the threaded portion 101 of transducer body 91. Transducer body 91 has a shoulder 142 forward of the threads of portion 101. Sleeve 141 is threaded onto portion 101 until it butts against shoulder 142. Internal sleeve 141 is sized so that when the handpiece 13 is assembled, its back end 143 is spaced forwardly of the back end of outer sleeve 71 as seen in FIGS. 3 and 8.

Internal sleeve 141 has an axially extending slot 145 extending forwardly from the sleeve's rear end 143, a pin hole 146 forwardly of slot 145, and an elongate, generally rectangular opening 147 formed forwardly of slot 145. Opening 147 is sized to allow access to wires 108 and 109 within the sleeve, to allow for connection of wires, as will be explained below. Slot 145 is sized to receive connector finger 21. Preferably, connector finger 21 and slot 145 are sized so that slot 145 is slightly expanded when finger 21 is forced into the slot, to provide a tight friction fit between the connector 11 and sleeve 141 to hold handpiece 13 to connector 11. Sleeve 141 is thus preferably made from a slightly flexible material.

A handpiece connector body 151 is force fit in internal sleeve 141, through the back of the sleeve. A lock pin 153 is fitted into a radial blind bore formed near the front of connector body 151. Pin 153 is sized to slide through pin hole 146 of internal sleeve 141, and functions to prevent pivotal or radial motion of the connector 151 with respect to the sleeve 141. Two axially extending through bores 155 and 157 are formed in connector body 151. Bore 157 is formed concentrically with the outer surface of body 151 and bores 155 are positioned radially between the outer surface of body 151 and bore 157. As shown in FIG. 8, a plurality of bores 155 may be formed concentrically around central bore 157.

Bore 155 receives an electrical plug 159 (FIG. 3). Plug 159 has a front portion 161 which is press fit into bore 155 and a narrower pin 163 which extends out the back of the connector to be received in socket 39 (FIG. 6) of electrical connector 31 in conduit connector 11. Wire 109 is secured to the front portion 161 to connect the piezoelectric crystals 111 to a source of electricity. Preferably, wire 109 is formed as two wires, a first wire, connected to piezoelectric crystals 111, extending rearwardly from transducer body 91, and a second wire extending forwardly from plug 159 which are joined inside of internal sleeve 141, as shown in FIG. 3. The opening 147 in internal sleeve 141 facilitates connection of the wires after the sleeve has been threaded onto the transducer body 91 and after the connector body 151 has been inserted into the sleeve 141. Electrical plugs 159 are placed in other bores 155 to connect ground wires 108 extending back from transducer body 91, to a ground, through conduit 5. Ground wires 108 are preferably made of two wires which are then connected together inside of inner sleeve 71, in the same manner as live wire 109. Although only one ground is required, two are preferred to guard against the possibility of one ground failing. If one ground fails, the second ground will protect the patient and dentist or hygienist from potential electrical shocks.

Connector body bore 157 is preferably a constant diameter bore which receives the back of fluid tube 129 and a needle 171. As shown, the back of tube 129 is stepped radially outwardly to form a back section 173 which may be force fitted into the front of bore 157. Alternatively, bore 157 may be stepped inwardly, to form the equivalent of section 173, and the tube 129 would be fitted into the reduced diameter section so formed.

Needle 171 includes a body 175 which is fitted into the back of bore 157 until the back of the body is approximately flush with the back of connector body 151. Needle body 175 preferably has an annular external groove or shoulder 177 formed at the front of the body. A nose 179 extends rearwardly from body 175 to be received in the flow path outlet of connector 11. Needle 171 has a through bore, which is preferably narrowed at the end of nose 179. The bore is in fluid communication with tube 129, so that fluid may flow into the handpiece through nose 157, tube 129, transducer body 91, transducer nut 119, and into the scaler tip 123.

A chamber 181 is formed in tube back portion 173 to house a one-way check valve 183. Check valve 183 is preferably a duck bill valve having a pair of opposing lips 185 which are separated or opened by water flowing forwardly through the valve, but which prevent water from flowing rearwardly out of the handpiece. Duck bill valve 183 has a base section 186 which is received on needle shoulder 177.

To assemble the handpiece, the piezoelectric crystals 111, spacer 113, and lock nut 115 are placed on the nose of transducer body 91 with the live wire 109 extending from the washer 113 through bore 107. The crystals and washers are secured in place with the transducer nut 119. Ground wires are inserted and secured in blind bores 110. The wires are placed into the internal sleeve 141 and the sleeve is secured to the threaded portion 101 of the transducer body 91. Connector body 151, with tube 129, is fitted into the back of internal sleeve 141, and the wires extending into the sleeve. The connector body is urged into the internal sleeve 141 until the front of tube 129 seats in transducer body bore 127. Pin 153 is inserted through hole 146 to positionally retain body 151 in sleeve 141. The wires extending forwardly from connector body 151 and wires extending rearwardly from transducer body are then connected to their respective counterparts. Lastly, the external sleeve is slid over the internal sleeve, and the shield is fitted over the transducer body and threaded onto the external sleeve 71.

To connect the handpiece 13 to conduit connector 11, connector 11 is simply slid into the back of the handpiece and the electrical plugs 171 will slide into the sockets 39 and the needle nose 179 will slide into the valve 51 to open the ball valve by urging ball 55 rearwardly. By aligning the connector finger 21 with the internal sleeve slot 145, the connectors will be aligned, thus facilitating the connection of the two parts.

When the needle nose 179 is inserted into the connector body valve, the nose 171 forms a seal with the first O-ring before the nose contacts the valve ball 55, to create a fluid tight seal before the valve is opened. As the nose 179 is inserted further into the connector, the nose will form a second fluid tight seal with the second O-ring 63 before it begins to push against the ball 55 to open the valve so that water may flow into the nose 179, through the handpiece, and out the scaler tip 123. When the handpiece 13 is removed from connector 11, for autoclaving, the valve works the same way, but in reverse. After the conduit connector valve is closed and the seal between nose 171 and O-ring 63 is broken, the outer O-ring 65 and the nose 171 continue to form a fluid tight seal. This use of the double seal ensures that a fluid tight seal will exist before the valve is opened and after the valve is closed to prevent leaking of water, which may occur if only one seal were used. This also reduces the possibility that water may migrate onto any of the electrical connectors while current is running through the electrical connectors.

Similarly, the use of the duck bill valve 183 in handpiece 13 prevents the rearward flow of water through the handpiece, to prevent leaking of water out the back of the handpiece. This serves a two-fold purpose. First, water will not leak out of the back of the handpiece onto a patient, dentist, or hygienist. Secondly, contaminated fluids will not flow back into conduit connector 11. If this were to happen, the connector would have to be autoclaved.

In view of the foregoing, it can be seen that scaler 1 uses an autoclavable handpiece 13 which is easily connected to, and removed from, a connector at the end of conduit 5. The autoclavable handpiece reduces the possibility of fluid leaking out of the handpiece or connector 11 onto a patient or onto a live electrical connector.

Variations, within the scope of the appended claims may be apparent to those skilled in the art. For example, rather than one long slot 145 in internal sleeve 141, the sleeve may be provided with a shorter slot which receives the connector finger 23 and an hole which receives lock pin 153 to prevent rotation of connector body 151 relative to sleeve 141. Tube 129 could be formed without the flaired ends. Fewer or more electrical connectors could be used, as is necessary. Rather than providing a separate hole 146 for handpiece connector pin 153, slot 147 could be extended forwardly to receive the pin as well as the conduit connector finger. These examples are merely illustrative.

I claim:

1. A dental scaler including a control unit, a hand piece assembly, and a conduit carrying fluid and electrical power to the handpiece assembly; the handpiece assembly including a conduit connector secured to an end of said conduit remote from the control unit and an autoclavable handpiece removably connectable to the connector;

said conduit connector including a connector housing containing an electrical terminal, a fluid flow path having an inlet and an outlet, and a valve in said fluid flow path; said valve having a valve body housing a valve seat and a valve member movable between an open position and a closed position, said valve being biased closed;

said autoclavable handpiece including
a transducer body defining a fluid flow path;
a scaler tip secured to an end of said transducer body in fluid communication with said transducer body fluid flow path;
a piezoelectric crystal mounted on said transducer body in operative contact with said tip to vibrate said tip when activated;
an external sleeve extending rearwardly from said transducer body;
a handpiece connector body housed in said external sleeve spaced rearwardly of said transducer body; said handpiece connector body defining a fluid flow path in communication with said transducer body fluid flow path, and having a fluid connector in said handpiece fluid flow path connectable to said conduit connector valve, and an electrical terminal connectable to said conduit connector electrical terminal;
a wire electrically connecting said piezoelectric crystal to said handpiece connector body electrical terminal.

2. The dental scaler of claim 1 wherein said conduit connector electrical terminal defines a socket and said handpiece connector body electrical terminal comprises a plug slidably insertable into said socket.

3. The dental scaler of claim 1 wherein said handpiece connector body fluid connector includes a rearwardly extending hollow needle, said needle being insertable into said conduit connector fluid flow path, said needle being of sufficient length to urge said valve member off said valve seat to open said conduit connector valve.

4. The dental scaler of claim 3 wherein said conduit connector defines a first seal and a second seal, said first and second seals being spaced apart; said handpiece connector body needle sealing against said first seal to create a fluid tight seal with said connector before said needle seals against said second seal.

5. The dental scaler of claim 4 wherein said first and second seals comprise O-rings.

6. The dental scaler of claim 4 wherein said conduit connector valve body has a guide path in which said valve member is movable, said guide path defining at least one slot so that fluid may flow around said valve member when said valve member is in said open position.

7. The dental scaler of claim 4 wherein said handpiece connector body includes a valve in said handpiece connector body fluid flow path.

8. The dental scaler of claim 7 wherein said handpiece valve is a one-way check valve positioned in said handpiece to prevent fluid from flowing rearwardly.

9. The dental scaler of claim 8 wherein said handpiece valve is a duck bill valve.

10. The dental scaler of claim 1 wherein said transducer body has a forward nose on which said piezoelectric crystal is mounted, said nose defining an axially extending external groove for receiving said wire to connect said piezoelectric crystal to said connector body electrical connector.

11. The dental scaler of claim 10 wherein said handpiece includes an internal sleeve received within said external sleeve, said internal sleeve receiving said handpiece connector body, said internal sleeve having a rear end spaced inwardly from a rear end of said external sleeve.

12. The dental scaler of claim 11 wherein said external sleeve has an inner diameter slightly larger than the outer diameter of said conduit connector, said external sleeve slidably receiving said conduit connector to removably connect said handpiece to said connector.

13. The dental scaler of claim 12 wherein said internal sleeve has a slot extending axially from a rear edge thereof, said conduit connector having an arm which is received in said slot, said arm and slot cooperating to align said fluid connectors and electrical terminals of said handpiece assembly.

14. The dental scaler of claim 11 wherein said internal sleeve defines an axially extending opening, said wire being exposed through said opening; said wire comprising a wire extending forwardly from said connector body and a wire extending rearwardly from said transducer body, said opening facilitating the connecting of said wires.

15. A dental scaler including a control unit, a hand piece assembly, and a conduit carrying fluid and electrical power to the handpiece assembly; the handpiece assembly including a conduit connector secured to an end of said conduit remote from the control unit and an autoclavable handpiece removably connectable to the conduit connector;

said conduit connector including a housing containing a connector body, said connector body extending forwardly of said connector housing and including:
an electrical socket;
a fluid flow path having an inlet, an outlet, and a valve in said fluid flow path; said valve having a valve body housing a valve seat and a valve member movable between an open position and a closed position, said valve being biased closed;

said connector housing having an arm extending over said connector body;

said autoclavable handpiece including
a hollow sleeve receiving at a back end thereof a handpiece connector body having a fluid connector and an electrical connector matable with the valve and socket, respectively, of said conduit connector body, said conduit connector body being slidably received in said handpiece sleeve; said sleeve extending rearwardly over said handpiece connector body and defining an axially extending slot sized to receive said connector housing arm;
a transducer body having at least one piezoelectric crystal in electrical communication with said electrical connector and a scaler tip in operative contact with said piezoelectric crystal and in fluid communication with said handpiece fluid connector.

16. The dental scaler of claim 15 wherein said handpiece sleeve is at least slightly flexible, said slot being sized such that when said connector housing arm is received in said slot, said slot is expanded to create a size-on-size fit to frictionally hold said connector to said handpiece.

17. The dental scaler of claim 16 wherein said handpiece sleeve is made of an autoclavable plastic.

* * * * *